(12) United States Patent
Anspach et al.

(10) Patent No.: US 7,971,728 B2
(45) Date of Patent: Jul. 5, 2011

(54) BONE FRAGMENT COLLECTOR

(75) Inventors: Thomas D. Anspach, Jupiter, FL (US); Stephen M. Bucina, Cocoa Beach, FL (US)

(73) Assignee: The Anspach Effort, Inc, Palm Beach Gardens, FL (US)

( * ) Notice: Subject to any disclaimer, the term of this patent is extended or adjusted under 35 U.S.C. 154(b) by 1292 days.

(21) Appl. No.: 11/363,602

(22) Filed: Feb. 28, 2006

(65) Prior Publication Data

US 2007/0203471 A1 Aug. 30, 2007

(51) Int. Cl.
*A61B 19/00* (2006.01)
*B01D 24/28* (2006.01)

(52) U.S. Cl. ...... 210/402; 604/4.01; 604/6.01; 604/6.09; 604/406; 210/645; 210/651; 210/780; 210/784; 210/321.67; 210/321.68; 210/330; 210/331; 210/346; 210/321.78; 210/403; 210/404; 210/405; 210/406; 210/98; 210/323.2; 210/456; 422/101; 422/501

(58) Field of Classification Search ............... 210/645, 210/651, 780, 784, 321.67, 321.68, 330, 210/331, 346, 321.78, 321.87, 323.2, 402–406, 210/456; 604/4.01, 6.01, 6.09, 406
See application file for complete search history.

(56) References Cited

U.S. PATENT DOCUMENTS

| | | | | |
|---|---|---|---|---|
| 2,038,921 A | * | 4/1936 | Blaufuss | 210/397 |
| 3,802,843 A | * | 4/1974 | Kim | 422/71 |
| 4,865,813 A | * | 9/1989 | Leon | 422/101 |
| 2004/0000605 A1 | | 1/2004 | McPherson et al. | |
| 2004/0155132 A1 | | 8/2004 | McPherson et al. | |

* cited by examiner

*Primary Examiner* — Krishnan S Menon
*Assistant Examiner* — Allison Gionta
(74) *Attorney, Agent, or Firm* — Norman Friedland

(57) ABSTRACT

A filtration system for collecting bone fragments during surgery performed on a patient includes a cylinder having a rotating disk with circumferential arms extending radially in the cylinder to define pockets. The rotating disk includes a longitudinal hub that carries an outlet connected to a central passageway formed in the disk. A plurality of apertures on the disk permit the liquid to flow into the passageway and through the outlet while the pockets retain the bone fragments. The disk is rotated to align circumferential spaced pockets to align with the inlet and outlet ports. The disks includes bearing surfaces that permit the rotation thereof and the arms are spaced from the cylinder inner surface to allow the flow of fluid in the event the pockets fill and clog the apertures and prevent flow into the outlet passage.

9 Claims, 3 Drawing Sheets

BONE FRAGMENT COLLECTOR

FEDERALLY SPONSORED RESEARCH

None

TECHNICAL FIELD

This invention relates to apparatus for sifting the blood and liquid from the body of a patient during a surgical procedure and particularly for apparatus for collecting the bone fragments from blood and/or liquid occasioned by a surgical procedure.

BACKGROUND OF THE INVENTION

As is well known in the medical technology, bone fragments have become increasingly important for repair, fusion and the like, so as to perform autologous bone grafts and other medical procedures using autogenous bone for achieving bone augmentation. For example, bone particles can be used to repair bone, such as in the skull or spinal vertebrae. This invention should not be confused with a bone mill that converts bone fragments for reducing the particle size by a grinding technique. This invention serves to filtrate the blood and liquid used in surgery to collect bone fragments that result from drilling or other medical procedures relating to the bone.

For example bone mills are disclosed in U.S. Pat. No. 6,287,312 granted on Sep. 11, 2001 to Clokie et al and entitled *ORAL CRANIOFACIAL BONE MILL* and in U.S. Application Nos. 2004/0155132 and 2004/0000605.

It is imperative in the process of collecting bone fragments in an ongoing operation that the flow of fluid from the body is not stopped. Hence, in the collecting process in accordance with this invention, notwithstanding a filling of the apparatus with bone fragments the flow of fluid will continue. Further this invention maximizes the collection of bone fragments by selectively locating blood collecting pockets in line with the fluid flowing from the patient. In addition the apparatus includes a handle for allowing the movement of pockets in an easy and convenient manner permitting the surgeon or operator to rotate the pockets to be in line with the flow path.

SUMMARY OF THE INVENTION

An object of this invention is to provide a filtration system for removal of bone fragments from a blood and/or liquid from the body of a patient during a surgical procedure.

A feature of this invention is to provide a cylindrical chamber for rotary supporting a rotary disk having a plurality of axially extending spars each extending to the inner periphery of the cylindrical chamber but space therefrom to allow the passage of fluid. The cylinder chamber includes an inlet port aligned with the selected pocket and the disk include a central passage aligned with the discharge port formed at one end of the disk. The disk includes an enlarged diameter portion formed on one end adjacent to the discharge port that snugly fits into the cylindrical chamber for closing off the end of the chamber and provides rotary movement to the pockets. The disk includes a plurality of apertures communicating the filtrated flow stream of liquid to discharge the same while retaining the bone fragments in the selected pockets. The inlet port and outlet port are connected to a vacuum system for drawing the contaminated flow stream from the body of the patient.

Another feature of this invention is to locate a post or the like on the outside surface of the cylinder to secure the cylinder when being used during the filtration procedure.

Another feature of this invention is to include an inlet port communicating with the respective pockets to add an additive or the like to the bone fragments.

Another feature of this invention is to provide an improved filtration system for collecting bone fragments during a surgical procedure and is characterized as being easy to set up and maintain and to use.

The foregoing and other features of the present invention will become more apparent from the following description and accompanying drawings.

These figures merely serve to further clarify and illustrate the present invention and are not intended to limit the scope thereof.

DETAILED DESCRIPTION OF THE INVENTION

As mentioned in the earlier paragraphs the fragments occasioned when a surgical procedure is performed on the bone mixes with the patient's blood and other fluids that may be utilized in the procedure. The preferred embodiment depicts a bone collector assembly that is made from a plastic material and includes a handle-like structure and holder for the unit. As one skilled in the art will appreciate these features are simply one of a myriad of ways for rotating the inner disk and supporting the cylinder and any other handle and support structure is contemplated within the scope of this invention. Suffice it to say that the salient feature of this invention is a disk with radial extending arms rotary supported in a cylinder chamber to define pockets for collecting the fragments and apertures formed in the hollow disk that permit the liquid to flow out of the chamber. The details of this invention is described immediately below.

Figure 1:
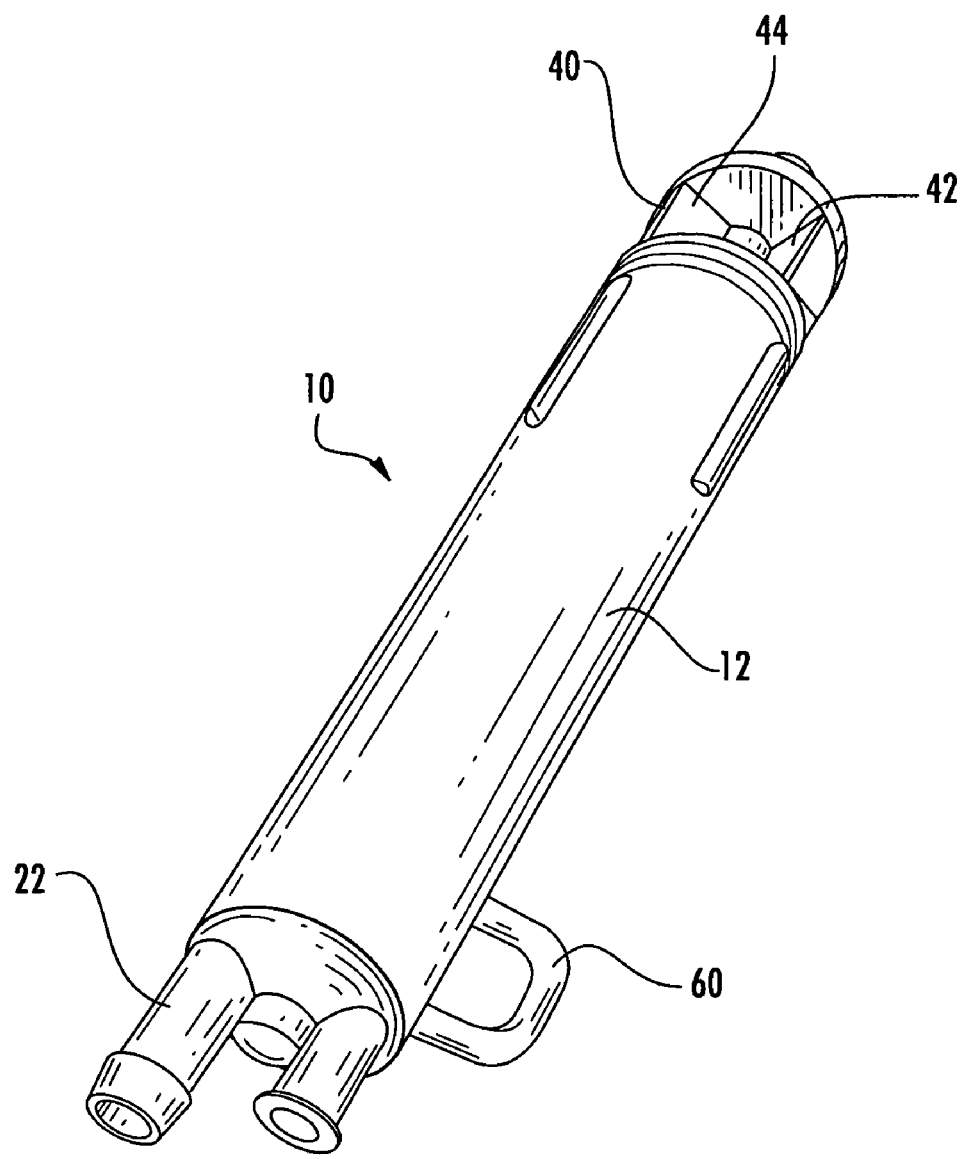
FIG. 1 is a view in perspective in elevation of the invention.
Figure 2:
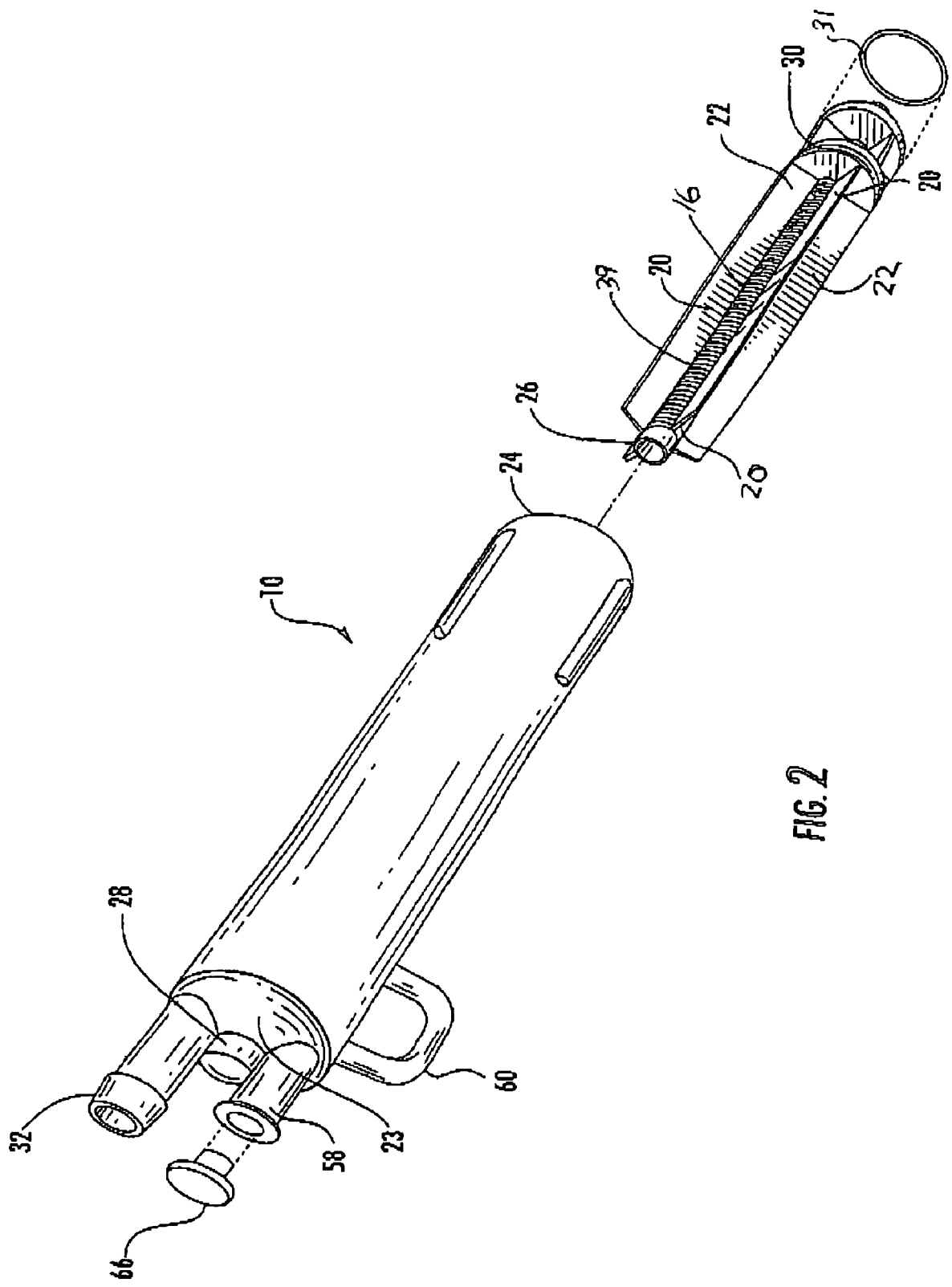
FIG. 2 is an exploded view of the embodiment depicted in FIG. 1.
Figure 3:
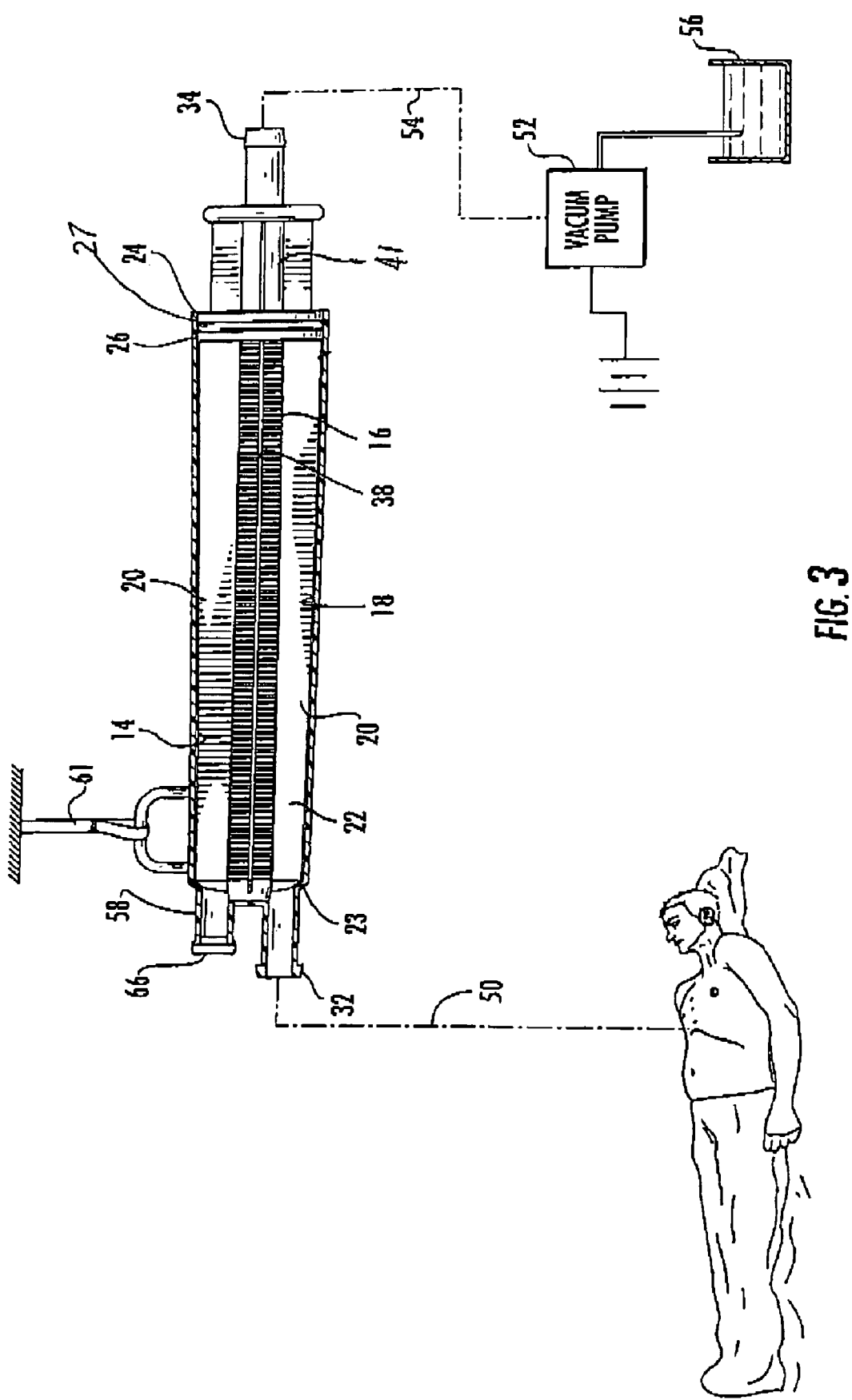
FIG. 3 is a sectional view taken along the longitudinal center and a schematic illustrating the detail of this invention.

As noted in FIGS. 1-3 the bone collector generally illustrated by reference numeral 10 comprises a cylindrical main body 12 defining a cylindrical chamber 14. A plurality of axially spaced hollow disks 16 are rotary supported in said cylindrical chamber and includes spaced radially extending longitudinal arms 20 extending toward the inner cylindrical surface 18 of chamber 14. The space between adjacent radially extending longitudinal arms 20 and including the adjacent spaced hollow disks 16 define spaced chambers or pockets 22. Each of said disks 16 are shaped like a commercially available washer and each are formed integrally with the longitudinal arms and extend radially inwardly. The hollow centers of each disk 16 align axially and form the central passageway 38.

cylindrical chamber 14 is closed on the fore end 23 and opened on the aft end 24. Disks 16 and its spaced longitudinal arms 20 fit into the cylindrical chamber 14 through the aft end 24. The assembly of the disks and spaced longitudinal arms 20 are rotatable within chamber 14 and removable from chamber 14. Integrally formed at the aft end of longitudinal arms is the annularly shaped portion 31 that includes the journal bearing surface 26 that snugly fits into the aft end of cylindrical chamber 14, journal surface 30 of of arms 20 snugly fits into the cylinder chamber 14 at the fore end of cylinder chamber 14 and extends to the journal bearing surface 26 and serves two functions. One, it rotary supports the arms 20 and disks 16 and two: it defines with adjacent arms 40 the pockets 22. The surface of bearings 26 bears against the inner surface 18 of the cylinder chamber 14 and is supported thereby and similarly, the bearing surface of the journal bearing 30 11 bears against the inner surface 18 of the cylindrical chamber 14 for rotary supporting said disks and journal bearing 30 cooperates with the inner surface 18 to form a seal. The chamber 14 includes an inlet port 32 mounted at the edge of the fore end 23 of the main body 12 and selectively aligns with each of the pockets 22 when rotated in alignment therewith.

The outlet 34 is located at the end of the disks 16 and communicates with the central openings in the disks 16 defining the central passageway 38 longitudinally extending from the closed aft end 41 to the outlet port 34. Each pocket 22 includes a plurality of apertures defined by the space 39 between adjacent disks 16 that fluidly connect the pocket with the central passageway 38.

Extending from the aft end of disk 16 includes is a larger diameter portion 40 that serves as a handle 42 that may include blade-like elements 44 that are carried or integrally formed to allow for the surgeon or operator to easily rotate the disk 16 to selectively align the pockets 22 with the inlet port 32.

In operation, With the suction pump in the on position and the tube is connected to the cavity of the patient the fluid and bone fragments from the cavity flows into the inlet 66 then, into one of the pockets 22 and then the fluid flows through the space or apertures 39 between disks 16 and through the central hole in the disks and then to the tank 56 via passage 41 and through the outlet 34 and line 54. The bone fragments that are larger than the space 39 will be collected and held in the respective pocket until emptied by the operator. It is abundantly important that the flow of fluid from the patient is not interrupted. To this end the arms 20 of disk 16s extend radially toward the inner surface 18 of the chamber 14 but a slightly spaced there from. Hence, in the event a pocket becomes filled and blocks the flow of fluid through the apertures 39 the flow of fluid will flow freely through the space between the end of the arms 20 and the inner surface 18 of chamber 14.

It is apparent from the fore going that the bone fragments will be collected in the pockets 22. The patient is hooked up to a suction pump and circuit that includes a hose 50 connected to the operation cite of the patient and fitted to the inlet port 32. The discharge port is connected to a commercially available suitable suction pump 52 via the hose 54. The affluent fluid is drained into the reservoir 56 while the bone fragments remain in the pockets 22. As each pocket fills up with bone fragments the operator rotates the disk to align the empty pocket with the suction circuit.

The extension 60 in the shape of a U is formed on the outer surface of the main body 12 and serves to support the main body by a suitable strap 61 attached to a suitable stand or the like. A port 58 may be included if desired which can be used to add additives to the bone fragments. End cap 66 may be used to close port 58 and obviously, removed when it is desired to use the same.

What has been shown is a uncomplicated apparatus for collecting bone fragments that is characterized as being simple to operate and maintain and is relatively inexpensive.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention It is claimed:

1. A filtration system for collecting bone fragments from a patient in the course of surgery comprising a cylinder having a cylindrical chamber, a plurality of spaced disks, radially and circumferentially spaced arms integrally attached to the outer circumference of said disks defining pockets in said cylinder chamber, the space between disks defining passageways for flowing liquid through central openings formed in said disks defining a central passageway to discharge the fluid while the bone fragments are retained in a selected pocket, and said pockets are selectively rotated to collect bone fragments and a suction pump connected to said cylinder for flowing the fluid and bone fragments from the patient.

2. A filtration system as claimed in claim 1 wherein said cylindrical chamber includes an inner surface and said arms having edges spaced from said inner surface to allow the flow of fluid to bypass said space in the event the pockets fill with fragments and clog said apertures.

3. A filtration system as claimed in claim 2 including an extension mounted on the cylinder for supporting the cylinder in relative position to the patient.

4. A filtration system as claimed in claim 3 including a handle attached to said disk for permitting the rotation of said disk.

5. Apparatus for collecting bone fragments from a stream of liquid including a main cylindrically shaped housing closed at one end and opened at the opposite end defining a chamber, a plurality of spaced disks rotary mounted in said chamber and having a plurality of radially extending arms circumferentially spaced around said disk and extending to but spaced from the inner surface of said chamber and defining therewith a plurality of pockets, said disks including a plurality of apertures allowing the passage of fluid to flow out of said pockets and said pockets collecting the bone fragments, an inlet port formed on one end of said cylinder for selectively leading the fluid and bone fragments into said pockets, and an outlet port formed on the end of said disk remote from the closed end of said main cylindrically shaped housing, said cylinder including a reduced diameter portion having a recess, a bearing on said disk in said recess for supporting said disk, an enlarged portion on said disk having a bearing surface being supported by said inner surface of said cylinder for rotary movement of said disk to selectively align said pockets for collecting bone fragments, whereby the operator rotates said disk to align said pockets with the inlet port.

6. Apparatus as claimed in claim 5 wherein said bearing surface at the opened end of said cylinder cooperate with the inner surface of said cylinder for
   providing seal to prevent the escape of liquid from said cylinder.

7. Apparatus as claimed in claim 6 including a projection formed on said outer diameter of said cylinder for supporting said cylinder when used in a surgical procedure.

8. Apparatus as claimed in claim 7 including a handle formed on one end of said disk extending from said opened end of said cylinder and capable of being handled by an operator to rotate said disk.

9. Apparatus as claimed in claim 8 including an additional inlet port selectively aligned with each of said plurality of pockets for adding an additive to said collected fragmented bones.

\* \* \* \* \*